United States Patent [19]

Kato et al.

[11] 4,413,047

[45] Nov. 1, 1983

[54] CADMIUM PHOTOCONDUCTOR WITH (DIALKYLPYROPHOSPHATO) ORGANIC TITANATE ADDITIVE

[75] Inventors: Yoshiaki Kato, Hirakata; Akira Fushida, Suita; Hideo Fukuda, Katano; Toru Nakazawa, Osaka; Yasushi Kamezaki, Sakai; Hideyuki Sasaki, Morioka, all of Japan

[73] Assignee: Mita Industrial Co., Ltd., Osaka, Japan

[21] Appl. No.: 367,252

[22] Filed: Apr. 12, 1982

[51] Int. Cl.³ .................. G03G 5/087; G03G 5/09
[52] U.S. Cl. ................................. 430/94; 430/95
[58] Field of Search ........................... 430/94, 95

[56] References Cited

U.S. PATENT DOCUMENTS 3,541,028 11/1970 Makino et al. ............... 430/95 X
3,598,760 8/1971 Nakamura et al. ........... 430/95 X
4,275,135 6/1981 Tomonaga ........................ 430/95

FOREIGN PATENT DOCUMENTS 56-065144 2/1981 Japan .

*Primary Examiner*—Roland E. Martin, Jr.
*Attorney, Agent, or Firm*—Sherman & Shalloway

[57] ABSTRACT

Disclosed is a photosensitive material for electrophotography comprising a conductive substrate and a layer of a composition comprising a dispersion of a photoconductive pigment in a binder resin, which is formed on the conductive substrate, wherein a (dialkypyrophosphato) organic titanate is incorporated into said composition.

This photosensitive material is excellent in the ozone resistance and the moisture resistance.

11 Claims, No Drawings

CADMIUM PHOTOCONDUCTOR WITH (DIALKYLPYROPHOSPHATO) ORGANIC TITANATE ADDITIVE

BACKGROUND OF THE INVENTION (1) Field of the Invention:

The present invention relates to a photosensitive material for electrophotography. More specifically, the present invention relates to a photosensitive material for electrophotography, which is excellent in the ozone resistance and the moisture resistance.

(2) Description of the Prior Art:

As one kind of a photosensitive plate for electrophotography, there has been widely used a photosensitive plate comprising a layer of a composition comprising a dispersion of a photoconductor in a binder resin, which is formed on a conductive substrate. When this photosensitive plate is used for electrophotography, the photosensitive plate is charged by corona discharge of a certain polarity and is then subjected to imagewise light exposure to form an electrostatic image, the electrostatic image is developed with a toner, the toner image is transferred on a copy sheet from the photosensitive plate, and the surface of the photosensitive plate is cleaned. This reproduction cycle is repeated.

Among photoconductive pigments used for such photosensitive plates, cadmium sulfide is especially excellent in the sensitivity. However, when a photosensitive plate comprising cadmium sulfide as the photoconductor is used for reproduction repeatedly for a long time under a high-humidity condition, the image density is drastically reduced.

Cadmium sulfide is an n-type photoconductor and hence, it is subjected to corona discharge of a negative polarity. Accordingly, the photosensitive layer is always attacked by ozone and is rendered sensitive to the humidity. It is construed that the initial charge potential is reduced for this reason.

SUMMARY OF THE INVENTION

We found that when a (dialkylpyrophosphato) organic titanate is incorporated in a photosensitive layer comprising a dispersion of a photoconductor such as cadmium sulfide in a binder resin such as an epoxy resin, the ozone resistance and moisture resistance of the photosensitive plate are prominently improved.

More specifically, in accordance with the present invention, there is provided a photosensitive material for electrophotography comprising a conductive substrate and a layer of a composition comprising a dispersion of a photoconductive pigment in a binder resin, which is formed on the conductive substrate, wherein a (dialkylpyrophosphato) organic titanate is incorporated into said composition.

DETAILED DESCRIPTION OF THE PREFERRED EMBODIMENTS

The high-humidity deterioration of the photosensitive plate due to the attack of ozone is confirmed by subjecting the photosensitive plate to the reproduction cycle of negative charging—light exposure—transfer—electricity removal repeatedly, allowing the treated photosensitive plate to stand under a high-humidity condition and measuring reduction of the charge potential. For example, when a photosensitive layer formed by dispersing a cadmium sulfide type photoconductor in a binder comprising an epoxy resin component and an amine type curing agent, which is considered to be most excellent in the moisture resistance, is subjected to the above-mentioned reproduction cycle 2000 times and then to the humidifying treatment at a temperature of 30° C. and a relative humidity of 80% for 12 hours, the ratio of reduction of the initial saturation charge potential of the photosensitive layer is as high as 75%. In contrast, if the (dialkylpyrophosphato) organic titanate is incorporated in the above-mentioned photosensitive layer, when the photosensitive layer is subjected to the above treatments, the ratio of reduction of the charge potential of the photosensitive layer is as low as about 5%. Accordingly, it is seen that the ozone resistance and the moisture resistance are prominently improved according to the present invention.

The (dialkylpyrophosphato) organic titanate that is used in the present invention has a chemical structural feature that is not observed in ordinary organic titanate type coupling agents. More specifically, an ordinary organic titanate contains an alkyl group or alkyl and acyl groups bonded to the titanium atom through the oxygen atom. The organic titanate having this structure has no substantial effect of preventing the high-humidity deterioration due to the attack of ozone. In contrast, the organic titanate used in the present invention is characterized in that it contains a dialkylpyrophosphato group bonded to the titanium atom, and by dint of this chemical structural feature, the organic titanate of the present invention has an excellent effect of preventing the high-humidity deterioration due to the attack of oxygen.

It is preferred that the organic titanate that is used in the present invention should have a structure represented by the following general formula:

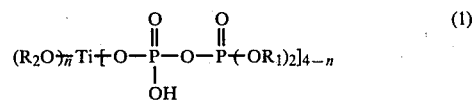

wherein n is an integer of rom 1 to 3, $R_1$ stands for an alkyl group, and $R_2$ stands for an alkyl group, an alkylene group or an alkylene-carbonyl group with the proviso that when n is 2, two of groups $R_2$ may be connected together to form an alkylene group or an alkylene-carbonyl group.

In the above general formula (1), it is preferred that the alkyl group $R_1$ be an alkyl group having 6 to 18 carbon atoms, such as an octyl group, a decyl group, a dodecyl group or a stearyl group. When the group $R_2$ is an alkyl group, it is preferred that the alkyl group be an alkyl group having 2 to 6 carbon atoms, such as an ethyl group, an isopropyl group, an n-butyl group, an isobutyl group or a sec-butyl group. It is especially preferred that n be 1 or 2, that is, the organic titanate be a bis- or tris-(dialkylpyrophosphato) organic titanate. When n is 2 and two groups $R_2$ are connected together to form an alkylene or alkylene-carbonyl group, as the alkylene group, there can be mentioned an ethylene group ($-CH_2-CH_2-$), and as the alkylene-carbonyl group, there can be mentioned a methyl-carbonyl group

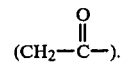

According to the present invention, a prominent effect can be obtained when a photoconductive pigment to be charged by negative corona discharge, especially a photoconductor showing extreme reduction of the moisture resistance by the ozone treatment, that is, a cadmium sulfide type photoconductor, is used as the photoconductor. Any of cadmium sulfide type photoconductors known in the field of electrophotography can be used in the present invention. It is known that cadmium sulfide can be activated or sensitized by copper or chlorine. Particles of a CdS photoconductor sensitized by copper or the like is especially advantageously used for attaining the objects of the present invention. Instead of cadmium sulfide as the single substance, there may be used cadmium selenide sulfide, that is, CdS—CdSe solid solution, may be used in the state activated by copper or the like.

As the binder resin, there can be used a known binder resin excellent in the resistance to the high-humidity deterioration due to the attack of ozone, especially a combination of an epoxy resin component and a curing agent component.

In the present invention, a known epoxy resin component having at least two oxirane rings can be used as the epoxy resin component. Preferred examples are described below though epoxy resins that can be used in the present invention are not limited to those exemplified below.

Glycidyl ether type epoxy resins:

Epoxy resins derived from polyfunctional hydroxyl group-containing compounds such as bisphenol A, brominated bisphenol A, bisphenol F, tetrahydroxyphenylethane, resorcinol, novolak, polyalkylene glycol and glycerin and epihalohydrins.

Glycidyl ester type epoxy resins:

Glycidyl phthalate, glycidyl hexahydrophthalate and glycidyl ester of dimer acid.

Glycidyl amines:

Triglycidyl isocyanurate and tetraglycidyldiaminodiphenylmethane.

Alicyclic epoxy resins:

3,4-Epoxy-6-methylcyclohexyl methyl-3,4-epoxy-6-methylcyclohexane-carboxylate, vinylcyclohexene diepoxide, dicyclopentadiene oxide and bis(2,3-epoxycyclopentyl)ether.

A bisepoxide, especially a bisphenol type epoxide resin, having an epoxy equivalent of 150 to 500, particularly 150 to 300, is preferred as the epoxy resin component.

Although a curing agent such as an acid anhydride may be used as the curing agent component, it is preferred that a low-temperature or medium-temperature curing agent, that is, an amine type curing agent, be used as the curing agent component. As preferred examples of the amine type curing agent, there can be mentioned aliphatic polyamines such as diethylene triamine, triethylene tetramine, diethylaminopropylamine, menthene diamine, N-aminoethylpiperazine, m-xylene diamine, 3,9-bis(3-aminopropyl)-2,4,8,10-tetraoxaspiro[5,5]undecane and bis(4-amino-3-methylcyclohexyl)methane, modified aliphatic polyamines such as epoxy resin-polyamine adducts, polyamine-ethylene oxide adducts, polyamine-propylene oxide adducts, cyanoethylated polyamines and ketone-blocked polyamines, and aromatic polyamines such as m-phenylene diamine, 4,4'-methylene dianiline and diaminophenylsulfone.

In the present invention, the epoxy resin component and the amine type curing agent component may be used at a known mixing ratio, for example, a weight ratio of from 100/1 to 100/200.

In the present invention, it is preferred that the (dialkylpyrophosphato) organic titanate be used in an amount of 0.05 to 5 parts by weight, especially 0.1 to 2 parts by weight, per 100 parts by weight of the photoconductive pigment. If the amount of the organic titanate is too small and below the above range, the desired deterioration-preventing effect cannot be obtained, and if the amount of the organic titanate is too large and beyond the above range, the sensitivity of the photosensitive layer tends to decrease.

In the present invention, it is preferred that the binder resin be used in an amount of 20 to 200 parts by weight, especially 30 to 150 parts by weight, per 100 parts by weight of the photoconductive pigment.

The photosensitive material of the present invention is prepared by dissolving or dispersing the epoxy resin component, the amine type curing agent component, the organic titanate type ozone deterioration-preventing agent and the CdS photoconductor in a solvent, for example, a cyclic ether such as tetrahydrofuran, a ketone such as methylethyl ketone, an aromatic solvent such as toluene or a halogenated hydrocarbon such as dichloroethane or monochlorobenzene and coating the resulting coating composition on a known conductive substrate.

The (dialkylpyrophosphato) organic titanate used in the present invention has a surface-active action and exerts a function of dispersing the CdS type photoconductor in a good condition in the coating composition. This is another prominent advantage of the present invention.

It is preferred that the solid concentration of the coating composition be 20 to 50% by weight, though the preferred concentration differs to some extent according to the coating method. It is preferred that the thickness of the photosensitive layer formed on the substrate be 10 to 100μ, especially 15 to 50μ, as solids.

The present invention will now be described in detail with reference to the following Examples that by no means limit the scope of the present invention.

EXAMPLE 1

| | |
|---|---|
| Cadmium sulfide powder (PC-108 supplied by Silvania Co.) | 8.0 g |
| Tetrahydrofuran | 4.0 g |
| Bisphenol type epoxy resin (epoxy equivalent of 192) | 2.6 g |
| Amine-adduct curing agent | 1.4 g |
| Titanate type coupling agent [bis(dioctylpyrophosphato) oxyacetate titanate] | 0.06 g |

The above ingredients precisely weighed were dispersed for 1 minute by an ultrasonic dispersing machine. The dispersion was coated on an aluminum sheet having a thickness of 80μ by a wire doctor blade and subjected to a heat curing treatment in an oven at 100° C. for 1 hour to obtain a photosensitive plate (No. 1) having a photosensitive layer thickness of 25μ after heating curing.

For comparison, a photosensitive plate (No. 2) was prepared in the same manner as described above except that the titanate type coupling agent was not added. Another comparative photosensitive plate (No. 3) was prepared in the same manner as described above except that an organic titanium compound, that is, tetraoctyl titanate, was used instead of the titanate type coupling agent used in Example 1.

These three photosensitive plates were allowed to stand in a thermostat tank maintained at a temperature of 30° C. and a relative humidity of 80% for 12 hours, and the charge quantities were measured by using a static copying paper tester (Model SP-428 supplied by Kawaguchi Denki K.K.) under the following conditions:

Measuring method: static measurement II
Applied voltage: −6 KV

The initial potentials (V1) of the three photosensitive plates measured according to the above method are shown in Table 1.

In order to effect the ozone treatment, each of the three photosensitive plates was set at a copying machine (Model DC-15 supplied by Mita Industrial Co., Ltd.) from which a development unit zone had been removed and the cycle of charging—exposure—transfer—removal of electricity was repeated 2000 times without passing a transfer sheet through the copying machine.

The ozone-treated photosensitive plates were allowed to stand in a thermostat tank maintained at a temperature of 30° C. and a relative humidity of 80% for 12 hours. After this humidifying treatment, the charge quantities of the photosensitive plates were measured in the same manner as described above.

The initial potentials (V2) after the ozone treatment and humidifying treatment are shown in Table 1. The ratio of reduction of the initial potential under the high-humidity condition by the ozone treatment was calculated from the values V1 and V2 to obtain results shown in Table 1.

For convenience, the initial potential reduction ratio is given by the following formula:

$$\text{Reduction ratio (\%)} = \frac{V1 - V2}{V1} \times 100$$

TABLE 1

| Sample No. | (V1) | (V2) | Reduction Ratio | Remarks |
| --- | --- | --- | --- | --- |
| 1 | 715V | 690V | 3.5% | present invention |
| 2 | 700V | 215V | 69.3% | comparison |
| 3 | 708V | 220V | 68.9% | comparison |

From the results shown in Table 1, it is seen that the charge quantity was hardly reduced in the photosensitive plate comprising the titanate type coupling agent though the charge quantity was drastically reduced in the photosensitive plate free of the titanate type coupling agent or the photosensitive plate comprising the organic titanium compound instead of the titanate type coupling agent. Thus, it has been confirmed that in the photosensitive plate according to the present invention, no substantial deterioration under a high-humidity condition by the ozone treatment is caused.

EXAMPLE 2

| | |
| --- | --- |
| Cadmium sulfide powder (PCP-MT supplied by Kasei Optonics Co.) | 8.0 g |
| Tetrahydrofuran | 4.0 g |
| Bisphenol type epoxy resin (epoxy equivalent of 200) | 2.9 g |
| Amine-adduct curing agent | 1.1 g |
| Titanate type coupling agent [isopropyltris(dioctylpyrophosphato)titanate] | 0.08 g |

The above ingredients precisely weighed were dispersed for 1 minute by an ultrasonic dispersing machine. The dispersion was coated on an aluminum sheet having a thickness of 80μ by a wire doctor blade and subjected to a heat curing treatment in an oven at 100° C. for 1 hour to obtain a photosensitive plate (No. 4) having a photosensitive layer thickness of 25μ after heat curing.

For comparison, a photosensitive plate (No. 5) was prepared in the same manner as described above except that the titanate type coupling agent was not added. Another comparative photosensitive plate (No. 6) was prepared in the same manner as described above except that an organic titanium compound, that is, tributyl chlorotitanate, was used instead of the titanate type coupling agent used in Example 2.

These three photosensitive plates were tested in the same manner as described in Example 1 to obtain results shown in Table 2.

TABLE 2

| Sample No. | (V1) | (V2) | Reduction Ratio | Remarks |
| --- | --- | --- | --- | --- |
| 4 | 655V | 627V | 4.3% | present invention |
| 5 | 635V | 135V | 78.7% | comparison |
| 6 | 641V | 140V | 78.1% | comparison |

From the results shown in Table 2, it is seen that the charge quantity was hardly reduced in the photosensitive plate comprising the titanate type coupling agent though the charge quantity was drastically reduced in the photosensitive plate free of the titanate type coupling agent or the photosensitive plate comprising the organic titanium compound instead of the titanate type coupling agent. Thus, it has been confirmed that in the photosensitive plate according to the present invention, no substantial deterioration under a high-humidity condition by the ozone treatment is caused.

EXAMPLE 3

| | |
| --- | --- |
| Cadmium sulfide powder (PCP-MT supplied by Kasei Optonics Co.) | 8.0 g |
| Tetrahydrofuran | 4.0 g |
| Bisphenol type epoxy resin (epoxy equivalent of 188) | 4.0 g |
| Amine-adduct curing agent | 1.5 g |
| Titanate type coupling agent [tris(dioctylpyrophosphato) ethylene titanate] | 0.04 g |

The above ingredients precisely weighed were dispersed for 1 minute by an ultrasonic dispersing machine. The dispersion was coated on an aluminum sheet having a thickness of 80μ by a wire doctor blade and subjected to a heat curing treatment in an oven at 100° C. for 1 hour to obtain a photosensitive plate (No. 7) having a photosensitive layer thickness of 25μ after heat curing.

For comparison, a photosensitive plate (No. 8) was prepared in the same manner as described above except that the titanate type coupling agent was not added. Another comparative photosensitive plate (No. 9) was prepared in the same manner as described above except that an organic titanium compound, that is, tetrabutyl titanate, was used instead of the titanate type coupling agent used in Example 3.

These photosensitive plates were tested in the same manner as described in Example 1 to obtain results shown in Table 3.

TABLE 3

| Sample No. | (V1) | (V2) | Reduction Ratio | Remarks |
|---|---|---|---|---|
| 7 | 697V | 660V | 5.3% | present invention |
| 8 | 665V | 167V | 74.8% | comparison |
| 9 | 671V | 178V | 73.5% | comparison |

From the results shown in Table 3, it is seen that the charge quantity was hardly reduced in the photosensitive plate comprising the titanate type coupling agent though the charge quantity was drastically reduced in the photosensitive plate free of the titanate type coupling agent or the photosensitive plate comprising the organic titanium compound instead of the titanate type coupling agent. Thus, it has been confirmed that in the photosensitive plate according to the present invention, no substantial deterioration under a high-humidity condition by the ozone treatment is caused.

What is claimed is:

1. A photosensitive material for electrophotography comprising a conductive substrate and a layer of a composition comprising a dispersion of a cadmium sulfide containing photoconductive pigment in a binder resin, which is formed on the conductive substrate, wherein 0.05 to 5 parts by weight per 100 parts by weight of the photoconductive pigment of a (dialkylpyrophosphato) organic titanate is incorporated into said composition.

2. A photosensitive material as set forth in claim 1, wherein the (dialkylpyrophosphato) organic titanate is a compound represented by the following general formula:

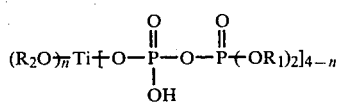

wherein n is an integer of from 1 to 3, $R_1$ stands for an alkyl group, and $R_2$ stands for an alkyl group, an alkylene group or an alkylene-carbonyl group with the proviso that when n is 2, two of groups $R_2$ may be connected together to form an alkylene group or an alkylene-carbonyl group.

3. A photosensitive material as set forth in claim 1, wherein the photoconductive pigment is a cadmium sulfide photoconductor.

4. A photosensitive material as set forth in claim 1, wherein the binder resin is a combination of an epoxy resin component and an amine type curing agent.

5. A photosensitive material as set forth in claim 4, wherein the epoxy resin component is a bisepoxide having an epoxy equivalent of 150 to 500.

6. A photosensitive material as set forth in claim 1, wherein the binder resin is present in an amount of 20 to 200 parts by weight per 100 parts by weight of the photoconductive pigment.

7. A photosensitive material as set forth in claim 1 wherein the photoconductive pigment is a cadmium selenide sulfide photoconductor.

8. A photosensitive material as set forth in claim 2 wherein $R_1$ is an alkyl group having 6 to 18 carbon atoms, $R_2$ is an alkyl group having 2 to 6 carbon atoms, n is 1 or 2 and when n is 2 the groups $R_2$ may be connected together to form an ethylene group or a methyl-carbonyl group.

9. A photosensitive material as set forth in claim 1 wherein the (dialkylpyrophosphato) organic titanate is selected from the group consisting of bis(dioctylpyrophosphato)oxy acetate titanate, isopropyl tris(dioctylpyrophosphato) titanate and tri(dioctylpyrophosphato)ethylene titanate.

10. A photosensitive material as set forth in claim 1 wherein the amount of the (dialkylpyrophosphato) organic titanate is from 0.1 to 2 parts by weight, per 100 parts by weight of the photoconductive pigment.

11. A photosensitive material as set forth in claim 2 wherein the photoconductive pigment is a cadmium sulfide photoconductor or a cadmium selenide sulfide photoconductor, and wherein the binder resin is a combination of an epoxy resin component and an amine type curing agent at a weight ratio of epoxy resin to curing agent of from 100/1 to 100/200, wherein the epoxy resin component is a bisepoxide having an epoxy equivalent of 150 to 500, said binder resin being present in an amount of 20 to 200 parts by weight per 100 parts by weight of the photoconductive pigment.

* * * * *

UNITED STATES PATENT AND TRADEMARK OFFICE
CERTIFICATE OF CORRECTION

PATENT NO. : 4,413,047
DATED : November 1, 1983
INVENTOR(S) : Yoshiaki Kato et al.

It is certified that error appears in the above-identified patent and that said Letters Patent is hereby corrected as shown below:

On the title page add:

-- [30]    Foreign Application Priority Data

Apr. 6, 1981    [JP]   Japan......56-50578        --.

Signed and Sealed this

Thirty-first Day of January 1984

[SEAL]

Attest:

GERALD J. MOSSINGHOFF

Attesting Officer    Commissioner of Patents and Trademarks